(12) United States Patent
Norden et al.

(10) Patent No.: US 6,610,650 B1
(45) Date of Patent: Aug. 26, 2003

(54) MODULATION OF CELLULAR TRANSCRIPTION FACTOR ACTIVITY

(75) Inventors: Benget Norden, Vastra Frolunda (SE); Pernilla Wittung, Gothenburg (SE); Ole Buchardt, Vaerlose (DK); Michael Egholm, Fredriksberg (DK); Peter E. Nielsen, Hjortevanget 509, DK 2980 Kokkedal (DK); Rolf Berg, Rungsted Kyst (DK)

(73) Assignee: Peter E. Nielsen (DK)

( * ) Notice: Subject to any disclaimer, the term of this patent is extended or adjusted under 35 U.S.C. 154(b) by 1 day.

(21) Appl. No.: 09/610,264

(22) Filed: Jul. 6, 2000

Related U.S. Application Data

(60) Division of application No. 08/088,661, filed on Jul. 2, 1993, now Pat. No. 6,228,982, which is a continuation-in-part of application No. 08/054,363, filed on Apr. 26, 1993, now Pat. No. 5,539,082, which is a continuation-in-part of application No. PCT/EP92/01219, filed on May 19, 1992.

(51) Int. Cl.[7] .......................... A01N 37/18; A01N 43/04
(52) U.S. Cl. .............................. 514/2; 436/501; 514/44
(58) Field of Search ...................... 514/44, 2; 436/63, 436/501; 435/6

(56) References Cited

PUBLICATIONS

Blackwell et al., "Sequence–Specific DNA Binding by the c–Myc protein," Science, 250:1149–1151, 1990.

Cullen et al., "The HIV–1 Tat Protein: An RNA Sequence–specific Processivity Factor, "Cell, 63:655–657, 1990.

Eckstein, F. ed. *Oligonucleotides and Analogues, A Practical Approach*, Ed.; 1991, IRL Press.

Franza, Jr. et al., "Characterization of Cellular proteins recognizing the HIV enhancer using a microscale DNA–affinity precipation assay," Nature, 330:391–395, 1987.

Gait, M.J., ed., *Oligonucleotide Synthesis, A Practical Approach*, 1984, IRL Press, Oxford, pp. iii–xiii.

Gilmore et al., "Different Localization of the Product of the v–rel Oncogene in chicken Fibroblasts and Spleen Cells Correlates with Transformation by REV–T," Cell, 44:791–800, 1986.

Konig et al., "Autoregulation of fos: the dyad symmetry element as the major target of repression," EMBO Journal, 8:2559–2566, 1989.

Nisen et al., "Enhanced Expression of the N–myc Gene in Wilms' Tumors," Cancer Research, 46:6217–622, 1986.

Vasseur et al., "Oligonucleotides: Synthesis of a Novel Methylhydroxylamine–Linked Nucleotide Dimer and Its Incorporation into Antisense Sequences," J. Am. Chem. Soc., 1992, 114, 4006–4007.

*Primary Examiner*—Ardin H. Marschel
(74) *Attorney, Agent, or Firm*—Woodcock Washburn LLP

(57) ABSTRACT

A novel class of compounds, known as peptide nucleic acids, form double-stranded structures with one another and with ssDNA. The peptide nucleic acids generally comprise ligands such as naturally occurring DNA bases attached to a peptide backbone through a suitable linker.

6 Claims, 3 Drawing Sheets

SEQUENCE LISTING

```
<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (3)..(4)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (5)..(5)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (6)..(7)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (8)..(8)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (9)..(9)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (10)..(10)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (11)..(11)
<223> OTHER INFORMATION: Heterocyclic base is attached to N-acetyl
```

```
        (2-aminoethyl) glycine through the N-acetyl
        group at position 1 of the base

<400> SEQUENCE: 1

Gly Xaa Xaa Xaa Xaa Xaa Xaa Xaa Xaa Xaa Xaa Lys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (3)..(4)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (5)..(5)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (6)..(7)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (8)..(8)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (9)..(9)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (10)..(10)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (11)..(11)
<223> OTHER INFORMATION: Heterocyclic base is attached to N-acetyl
        (2-aminoethyl) glycine through the N-acetyl
        group at position 1 of the base

<400> SEQUENCE: 2

Lys Xaa Xaa Xaa Xaa Xaa Xaa Xaa Xaa Xaa Xaa Gly
1               5                   10

<210> SEQ ID NO 3
<211> LENGTH: 27
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
```

```
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (3)..(4)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (5)..(5)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (6)..(7)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (8)..(8)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (9)..(9)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (10)..(10)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (11)..(17)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (18)..(18)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (19)..(19)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (20)..(20)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (21)..(22)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (23)..(23)
<223> OTHER INFORMATION: Heterocyclic base is attached to N-acetyl
      (2-aminoethyl) glycine through the N-acetyl group at position 9 of
      the base
<220> FEATURE:
<221> NAME/KEY: misc_feature
<222> LOCATION: (24)..(25)
<223> OTHER INFORMATION: Heterocyclic base is attached to N-acetyl
```

```
        (2-aminoethyl) glycine through the N-acetyl
        group at position 1 of the base
<220> FEATURE:
<221> NAME/KEY: misc_feature
<222> LOCATION: (26)..(26)
<223> OTHER INFORMATION: Heterocyclic base is attached to N-acetyl
        (2-aminoethyl) glycine through the N-acetyl
        group at position 9 of the base

<400> SEQUENCE: 3

Gly Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Lys
            20                  25

<210> SEQ ID NO 4
<211> LENGTH: 22
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (3)..(4)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (5)..(5)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (6)..(7)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (8)..(8)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (9)..(9)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (10)..(10)
<223> OTHER INFORMATION: Heterocyclic base is attached to N-acetyl
        (2-aminoethyl) glycine through the N-acetyl
        group at position 9 of the base
<220> FEATURE:
<221> NAME/KEY: misc_feature
<222> LOCATION: (11)..(12)
<223> OTHER INFORMATION: Heterocyclic base is attached to N-acetyl
        (2-aminoethyl) glycine through the N-acetyl
        group at position 1 of the base
<220> FEATURE:
<221> NAME/KEY: misc_feature
<222> LOCATION: (13)..(13)
<223> OTHER INFORMATION: Heterocyclic base is attached to N-acetyl
        (2-aminoethyl) glycine through the N-acetyl
        group at position 9 of the base
<220> FEATURE:
```

<221> NAME/KEY: misc_feature
<222> LOCATION: (14)..(14)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (15)..(15)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (16)..(17)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (18)..(18)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (19)..(20)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (21)..(21)
<223> OTHER INFORMATION: Xaa can be any naturally occurring amino acid

<400> SEQUENCE: 4

Gly Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Lys
            20

<210> SEQ ID NO 5
<211> LENGTH: 30
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (3)..(4)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (5)..(5)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (6)..(10)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (11)..(11)
<223> OTHER INFORMATION: Heterocyclic base is attached to N-acetyl
      (2-aminoethyl) glycine through the N-acetyl
      group at position 9 of the base

```
<220> FEATURE:
<221> NAME/KEY: misc_feature
<222> LOCATION: (12)..(12)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (13)..(13)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (14)..(20)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (21)..(21)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (22)..(22)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (23)..(23)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (24)..(25)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (26)..(26)
<223> OTHER INFORMATION: Heterocyclic base is attached to N-acetyl
      (2-aminoethyl) glycine through the N-acetyl
      group at position 9 of the base
<220> FEATURE:
<221> NAME/KEY: misc_feature
<222> LOCATION: (27)..(28)
<223> OTHER INFORMATION: Heterocyclic base is attached to N-acetyl
      (2-aminoethyl) glycine through the N-acetyl
      group at position 1 of the base
<220> FEATURE:
<221> NAME/KEY: misc_feature
<222> LOCATION: (29)..(29)
<223> OTHER INFORMATION: Heterocyclic base is attached to N-acetyl
      (2-aminoethyl) glycine through the N-acetyl
      group at position 9 of the base

<400> SEQUENCE: 5

Gly Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Lys
            20                  25                  30

<210> SEQ ID NO 6
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(25)
```

-continued

```
<223> OTHER INFORMATION: /note= "biotin labeled"

<400> SEQUENCE: 6 gatccccca ccacgtggtg cctga                                              25

<210> SEQ ID NO 7
<211> LENGTH: 25
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (25)..(25)
<223> OTHER INFORMATION: /note= "biotin labeled"

<400> SEQUENCE: 7
gatctcaggc accacgtggt ggggg                                             25
```

MODULATION OF CELLULAR TRANSCRIPTION FACTOR ACTIVITY

RELATED APPLICATION

This patent application is related to U.S. Pat. No. 5,641,625. This patent application also is a divisional of Ser. No. 08/088,661 now U.S. Pat. No. 6,228,982, filed Jul. 2, 1993, which is a continuation-in-part of Ser. No. 08/054,363 now U.S. Pat. No. 5,539,082, filed Apr. 26, 1993, which is a continuation-in-part of application PCT EP92/01219, filed May 19, 1992 and published Nov. 26, 1992 as WO 92/20702. The entire contents of each of the foregoing patent applications are incorporated herein by reference.

FIELD OF THE INVENTION

This invention is directed to generally linear compounds or "strands" wherein naturally-occurring nucleobases or other nucleobase-binding moieties preferably are covalently bound to a polyamide backbone. In particular, the invention concerns compounds wherein two such strands coordinate through hydrogen bonds to form a DNA-like double strand.

BACKGROUND OF THE INVENTION

The transcription and processing of genomic duplex DNA is controlled by generally proteinaceous transcription factors that recognize and bind to specific DNA sequences. One strategy for the control of gene expression is to add to a cell double-stranded DNA or double-stranded DNA-like structures that will bind to the desired factor in preference to or in competition with genomic DNA, thereby inhibiting processing of the DNA into a protein. This modulates the protein's action within the cell and can lead to beneficial effects on cellular function. Naturally occurring or unmodified oligonucleotides are unpractical for such use because they have short in vivo half-lives and they are poor cell membrane penetrators.

These problems have resulted in an extensive search for improvements and alternatives. In order to improve half-life as well as membrane penetration, a large number of variations in polynucleotide backbones has been undertaken. These variations include the use of methylphosphonates, phosphoro-thioates, phosphordithioates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives. The great majority of these backbone modifications lead to decreased stability for hybrids formed between the modified oligonucleotide and its complementary native oligonucleotide, as assayed by measuring $T_m$ values.

Consequently, there remains a need in the art for stable compounds that can form double-stranded, helical structures mimicking double-stranded DNA.

OBJECTS OF THE INVENTION

It is one object of the present invention to provide compounds that mimic the double-helical structure of DNA.

It is a further object of the invention to provide compounds wherein linear, polymeric strands coordinate through hydrogen bonds to form double helices.

It is another object to provide compounds wherein naturally-occurring nucleobases or other nucleobase-binding moieties are covalently bound to a non-sugar-phosphate backbone.

It is yet another object to provide therapeutic, diagnostic, and prophylactic methods that employ such compounds.

SUMMARY OF THE INVENTION

The present invention provides a novel class of compounds, known as peptide nucleic acids (PNAs), that can coordinate with one another or with single-stranded DNA to form double-stranded (i.e., duplex) structures. The compounds include homopolymeric PNA strands and heteropolymeric PNA strands (e.g., DNA/PNA strands), which coordinate through hydrogen bonding to form helical structures. Duplex structures can be formed, for example, between two complementary PNA or PNA/DNA strands or between two complementary regions within a single such strand.

In certain embodiments, each strand of the double-stranded compounds of the invention includes a sequence of ligands covalently bound by linking moieties and at least one of said linking moieties comprising an amide, thioamide, sulfinamide or sulfonamide linkage. The ligands on one strand hydrogen bond with ligands on the other strand and, together, assume a double helical structure. The compounds of the invention preferably comprise ligands linked to a polyamide backbone. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, 5-propynylthymine, etc.) attached to a peptide backbone through a suitable linker. These ligands are linked to the polyamide backbone through aza nitrogen atoms or through amido and/or ureido tethers.

In certain preferred embodiments, the peptide nucleic acids of the invention have the general formula (I):

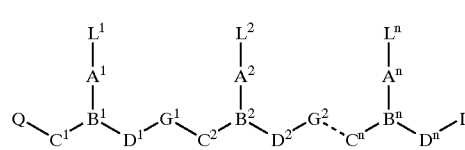

wherein:

n is at least 2, each of $L^1$–$L^n$ is independently selected from the group consisting of hydrogen, hydroxy, ($C_1$–$C_4$)alkanoyl, naturally occurring nucleobases, non-naturally occurring nucleobases, aromatic moieties, DNA intercalators, nucleobase-binding groups, heterocyclic moieties, and reporter ligands, at least one of $L^1$–$L^n$ being a naturally occurring nucleobase, a non-naturally occurring nucleobase, a DNA intercalator, or a nucleobase-binding group;

each of $C^1$–$C^n$ is $(CR^6R^7)_y$ where $R^6$ is hydrogen and $R^7$ is selected from the group consisting of the side chains of naturally occurring alpha amino acids, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen, ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

each of $D^1$–$D^n$ is $(CR^6R^7)$ where $R^6$ and $R^7$ are as defined above;

each of y and z is zero or an integer from 1 to 10, the sum y+z being greater than 2 but not more than 10;

each of $G^1$–$G^{n-1}$ is —$NR^3CO$—, —$NR^3CS$—, —$NR^3SO$— or —$NR^3SO_2$—, in either orientation, where $R^3$ is as defined above;

each pair of $A^1$–$A^n$ and $B^1$–$B^n$ are selected such that:
(a) A is a group of formula (IIa), (IIb) or (IIc) and B is N or $R^3N^+$; or
(b) A is a group of formula (IId) and B is CH;

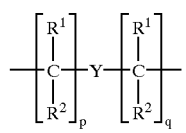
(IIa)

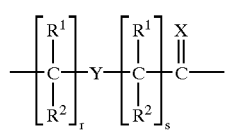
(IIb)

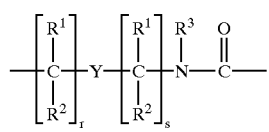
(IIc)

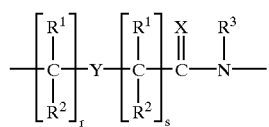
(IId)

where:

X is O, S, Se, $NR^3$, $CH_2$ or $C(CH_3)_2$;

Y is a single bond, O, S or $NR^4$;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, $(C_1$–$C_4)$alkyl which may be hydroxy- or alkoxy- or alkylthio-substituted, hydroxy, alkoxy, alkylthio, amino and halogen;

each of $G^1$–$G^{n-1}$ is —$NR^3CO$—, —$NR^3CS$—, —$NR^3SO$— or —$NR^3SO_2$—, in either orientation, where $R^3$ is as defined above;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

In certain embodiments, at least one A is a group of formula (IIc) and B is N or $R^3N^+$. In other embodiments, A is a group of formula (IIa) or (IIb), B is N or $R^3N^+$, and at least one of y or z is not 1 or 2.

Preferred peptide nucleic acids have general formula (IIIa)–(IIIc):

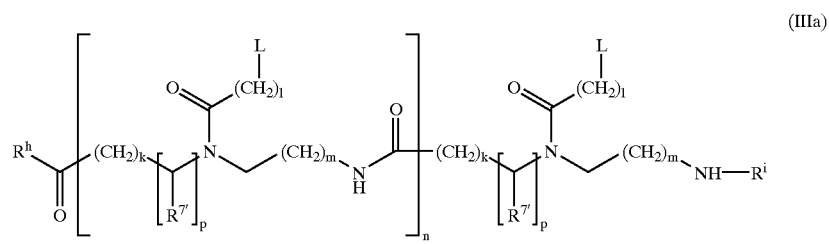
(IIIa)

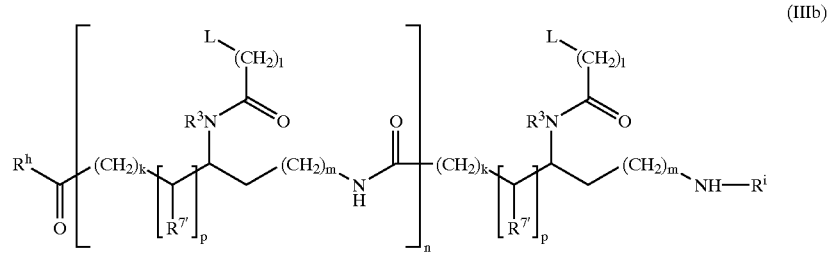
(IIIb)

-continued

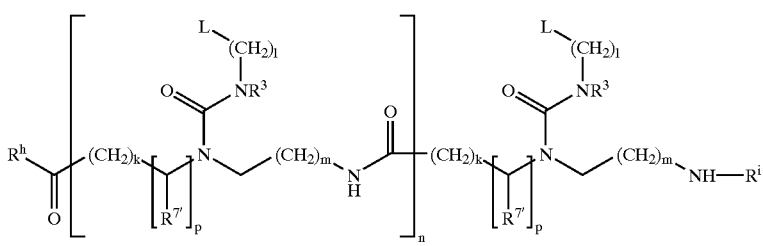

(IIIc)

wherein:
- each L is independently selected from the group consisting of hydrogen, phenyl, heterocyclic moieties, naturally occurring nucleobases, and non-naturally occurring nucleobases;
- each $R^{7'}$ is independently selected from the group consisting of hydrogen and the side chains of naturally occurring alpha amino acids;
- n is an integer from 1 to 60;
- each of k, l, and m is independently zero or an integer from 1 to 5;
- p is zero or 1;
- $R^h$ is OH, $NH_2$ or —$NHLysNH_2$; and
- $R^i$ is H or $COCH_3$.

Particularly preferred are compounds having formula (IIIa)–(IIIc) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20.

The peptide nucleic acids of the invention are synthesized by adaptation of standard peptide synthesis procedures, either in solution or on a solid phase. The synthons used are monomer amino acids or their activated derivatives, protected by standard protecting groups. The PNAs also can be synthesized by using the corresponding diacids and diamines.

Thus, the novel monomer synthons according to the invention are selected from the group consisting of amino acids, diacids and diamines having general formulae:

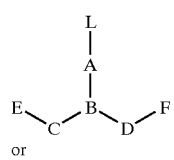

(IV)

or

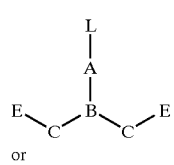

(V)

or

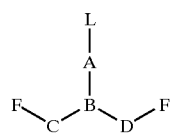

(VI)

wherein L, A, B, C and D are as defined above, except that any amino groups therein may be protected by amino protecting groups; E is COOH, CSOH, SOOH, $SO_2OH$ or an activated derivative thereof; and F is $NHR^3$ or $NPgR^3$, where $R^3$ is as defined above and Pg is an amino protecting group.

Preferred monomer synthons according to the invention have formula (VIIIa)–(VIIIc):

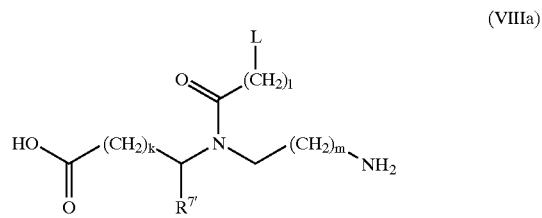

(VIIIa)

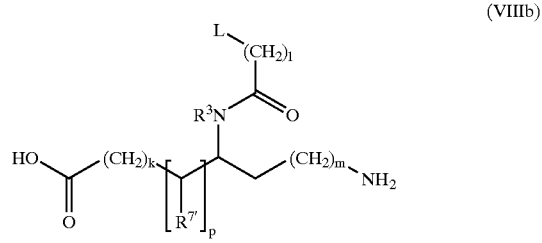

(VIIIb)

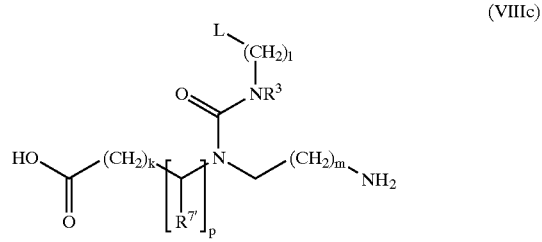

(VIIIc)

or amino-protected and/or acid terminal activated derivatives thereof, wherein L is selected from the group consisting of hydrogen, phenyl, heterocyclic moieties, naturally occurring nucleobases, and non-naturally occurring nucleobases; and $R^{7'}$ is selected from the group consisting of hydrogen and the side chains of naturally occurring alpha amino acids.

These compounds are able to recognize one another to produce double helices. Such recognition can span sequences 5–60 base pairs long. Sequences between 10 and 20 bases are of interest since this is the range within which unique DNA sequences of prokaryotes and eukaryotes are found. Sequences between 17–18 bases are of particular interest since this is the length of unique sequences in the human genome.

Thus, in one aspect, the present invention provides methods for modulating the activity of a transcription factor in a cell, comprising the steps of forming a PNA-containing double strand that binds the transcription factor and introducing the double strand into the cell.

Further, the invention provides methods for modulating the activity of a protein in a cell, comprising the steps of forming a PNA-containing double strand that binds to or suppresses expression of the protein and introducing the double strand into the cell.

The PNA duplex structures of the invention mimic dsDNA and can be used in diagnostics, therapeutics and as research reagents and kits. They can be used in pharmaceutical compositions by including a suitable pharmaceutically acceptable diluent or carrier.

BRIEF DESCRIPTION OF THE FIGURES

The numerous objects and advantages of the present invention may be better understood by those skilled in the art by reference to the accompanying figures, in which.

DETAILED DESCRIPTION OF THE INVENTION

As will be recognized, a variety of double-stranded (i.e., duplex) PNA-containing structures can be prepared according to the present invention. Representative duplexes can be formed within a single homopolymeric PNA strand or a single heteropolymeric strand (e.g., a chimera PNA-DNA or PNA-RNA strand), or between two homopolymeric PNA strands, two heteropolymeric PNA strands, or a homopolymeric PNA strand and a heteropolymeric PNA strand.

Figure 2:
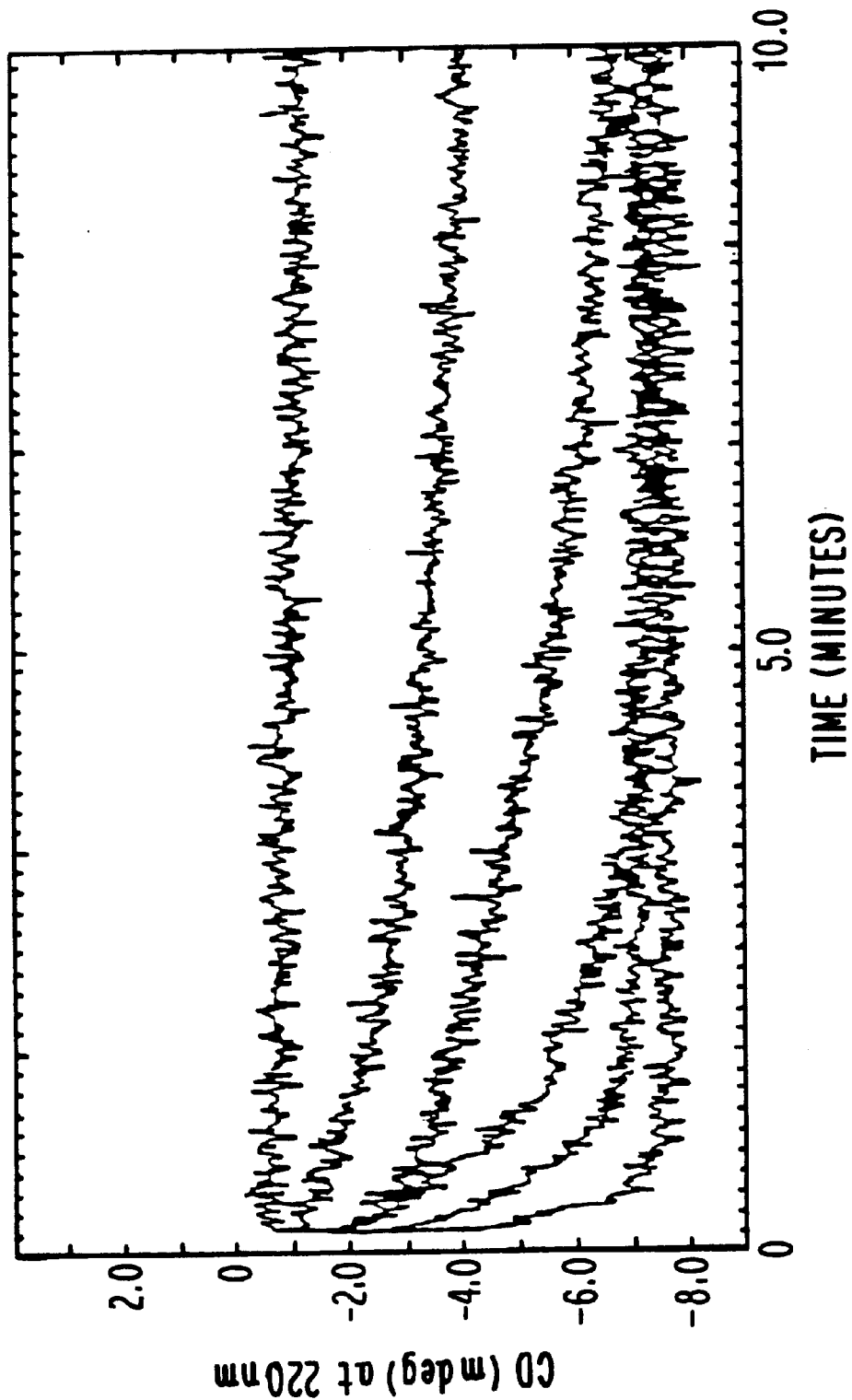
FIG. 2 is the development in time of the circular dichroism signal of certain compounds of the invention.

Each PNA strand or PNA portion of a chimera strand preferably comprises a plurality of ligands, L, linked to a backbone via attachment at the position found in nature, i.e., position 9 for adenine or guanine, and position 1 for thymine or cytosine. Alternatively, L can be a non-naturally occurring nucleobase (nucleobase analog), another base-binding moiety, an aromatic moiety, $(C_1-C_4)$alkanoyl, hydroxy or even hydrogen. It will be understood that the term nucleobase includes nucleobases bearing removable protecting groups. Some typical nucleobase ligands and illustrative synthetic ligands are shown in FIG. 2 of WO 92/20702. Furthermore, L can be a DNA intercalator, a reporter ligand such as, for example, a fluorophor, radio label, spin label, hapten, or a protein-recognizing ligand such as biotin. In monomer synthons, L can be blocked with protecting groups, as illustrated in FIG. 4 of WO 92/20702.

Linker A can be a wide variety of groups such as $-CR^1R^2CO-$, $-CR^1R^2CS-$, $-CR^1R^2CSe-$, $-CR^1R^2CNHR^3-$, $-CR^1R^2C=CH_2-$ and $-CR^1R^2C=C(CH_3)_2-$, where $R^1$, $R^2$ and $R^3$ are as defined above. Preferably, A is methylenecarbonyl $(-CH_2CO-)$, amido $(-CONR^3-)$, or ureido $(-NR^3CONR^3-)$. Also, A can be a longer chain moiety such as propanoyl, butanoyl or pentanoyl, or corresponding derivative, wherein O is, replaced by another value of X or the chain is substituted with $R^1R^2$ or is heterogenous, containing Y. Further, A can be a $(C_2-C_6)$alkylene chain, a $(C_2-C_6)$alkylene chain substituted with $R^1R^2$ or can be heterogenous, containing Y. In certain cases, A can just be a single bond.

In one preferred form of the invention, B is a nitrogen atom, thereby presenting the possibility of an achiral backbone. B can also be $R^3N^+$, where $R^3$ is as defined above, or CH.

In the preferred form of the invention, C is $-CR^6R^7-$, but can also be a two carbon unit, i.e. $-CHR^6CHR^7-$ or $-CR^6R^7CH_2-$, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In a preferred form of the invention, E in the monomer synthon is COOH or an activated derivative thereof, and G in the oligomer is $-CONR^3-$. As defined above, E also can be CSOH, SOOH, $SO_2OH$ or an activated derivative thereof, whereby G in the oligomer becomes $-CSNR^3-$, $-SONR^3-$ and $-SO_2NR^3-$, respectively. The activation can, for example, be achieved using an acid anhydride or an active ester derivative, wherein hydrogen in the groups represented by E is replaced by a leaving group suited for generating the growing backbone.

The amino acids which form the backbone can be identical or different. We have found that those based on 2-aminoethyl-glycine are especially well suited to the purpose of the invention.

In some cases it may be of interest to attach ligands at either terminus (Q, I) to modulate other properties of the PNAs. Representative ligands include DNA intercalators or basic groups, such as lysine or polylysine. Further groups such as carboxy and sulfo groups could also be used. The design of the synthons further allows such other moieties to be located on non-terminal positions.

Duplexes according to the present invention can be assayed for their specific binding activity to a transcription factor. As used herein, the term "binding affinity" refers to the ability of a duplex to bind to a transcription factor via hydrogen bonds, van der Waals interactions, hydrophobic interactions, or otherwise. For example a duplex can bind to a "leucine zipper" transcription factor or a helix-loop-helix transcription factor via positively charged amino acids in one region of the transcription factor.

Transcription factors, as the term is used herein, are DNA- or RNA-binding proteins that regulate the expression of genes. HIV tat and c-rel are examples of transcription factors which regulate the expression of genes. Also encompassed by the term are DNA and RNA binding proteins which are not strictly considered transcription factors, but which are known to be involved in cell proliferation. These transcription factors include c-myc, fos, and jun. Methods of the present invention are particularly suitable for use with transcription factor as target molecules since transcription factors generally occur in very small cellular quantities.

The compounds of the present invention also may be useful to bind to other target molecules. Target molecules of the present invention can include any of a variety of biologically significant molecules. Such other target molecules can be nucleic acid strands such as significant regions of DNA or RNA. Target molecules also can be carbohydrates, glycoproteins or other proteins. In some preferred embodiments of the present invention, the target molecule is a protein such as an immunoglobulin, receptor, receptor binding ligand, antigen or enzyme and more specifically can be a phospholipase, tumor necrosis factor, endotoxin, interleukin, plasminogen activator, protein kinase, cell adhesion molecule, lipoxygenase, hydrolase or transacylase. In other embodiments of the invention the target molecules can be important regions of the human immunodeficiency virus, Candida, herpes viruses, papillomaviruses, cytomegalovirus, rhinoviruses, hepatitises, or influenza viruses. In yet other embodiments of the present invention the target molecules can be regions of an oncogene. In still further embodiments, the target molecule is ras 47-mer stem loop RNA, the TAR element of human immunodeficiency virus or the gag-pol stem loop of human immunodeficiency virus (HIV). Still other targets can induce cellular activity. For example, a target can induce interferon.

In binding to transcription factors or other target molecules, the transcription factor or other target molecule need not be purified. It can be present, for example, in a whole cell, in a humoral fluid, in a crude cell lysate, in serum or in other humoral or cellular extract. Of course, purified transcription factor or a purified form of an other target moleucle is also useful in some aspects of the invention.

In still other embodiments of the present invention, synthetically prepared transcription factor or other target moleucle can be useful. A transcription factor or other target moleucle also can be modified, such as by biotinylation or radiolabeling. For example, synthetically prepared transcription factor can incorporate one or more biotin molecules during synthesis or can be modified post-synthesis.

An illustrative series of PNA oligomers according to the invention can be prepared as described in Example 1 below and have been designed as follows:

(1) Formulas 1 (SEQ ID NO:1) and 2 (SEQ ID NO:2), two complementary antiparallel PNA decamers that are not self-complementary:

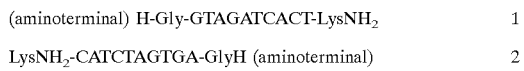

(aminoterminal) H-Gly-GTAGATCACT-LysNH$_2$     1

LysNH$_2$-CATCTAGTGA-GlyH (aminoterminal)     2

(2) Formula 3 (SEQ ID NO:3), a single PNA oligomer possessing a self-complementary motif ten base pairs long with an intervening loop region containing five base units:

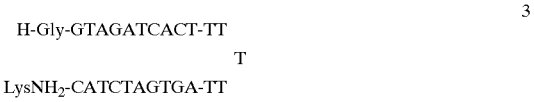

H-Gly-GTAGATCACT-TT
                    T
LysNH$_2$-CATCTAGTGA-TT

3

(3) Formula 4 (SEQ ID NO:4), a single PNA oligomer possessing a self complementary motif of ten base pairs long linked by an oligomethylene (n=1–10) spacer:

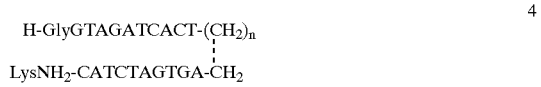

H-GlyGTAGATCACT-(CH$_2$)$_n$
                           |
LysNH$_2$-CATCTAGTGA-CH$_2$

4

(4) Formula 5 (SEQ ID NO:5), a single PNA oligomer possessing a self-complementary motif ten base pairs long on one side interrupted by a three base bulge and an intervening loop region containing five base units:

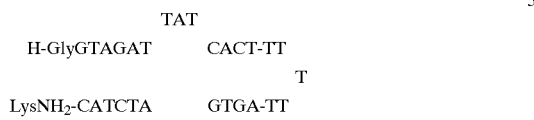

TAT
H-GlyGTAGAT     CACT-TT
                       T
LysNH$_2$-CATCTA     GTGA-TT

5

In each of the foregoing, LysNH$_2$ is intended to indicate that a lysine-amide is attached to the carboxyl end of the PNA. Use of such lysine-amide is not necessary; however, its use is preferred since it is believed to suppress aggregation of the oligomers. The aminoterminal end of the PNA is substituted with a glycine residue to avoid migration of the N-terminal nucleobase. The PNA amino-terminal and carboxy-terminal ends are intended to correspond, respectively, to the 5'-ends and 3'-ends of DNA. As a consequence of the designed sequences, these PNAs form duplexes having DNA-like antiparallel orientations. These PNAs additionally are capable of adopting a tertiary structure.

Figure 1:
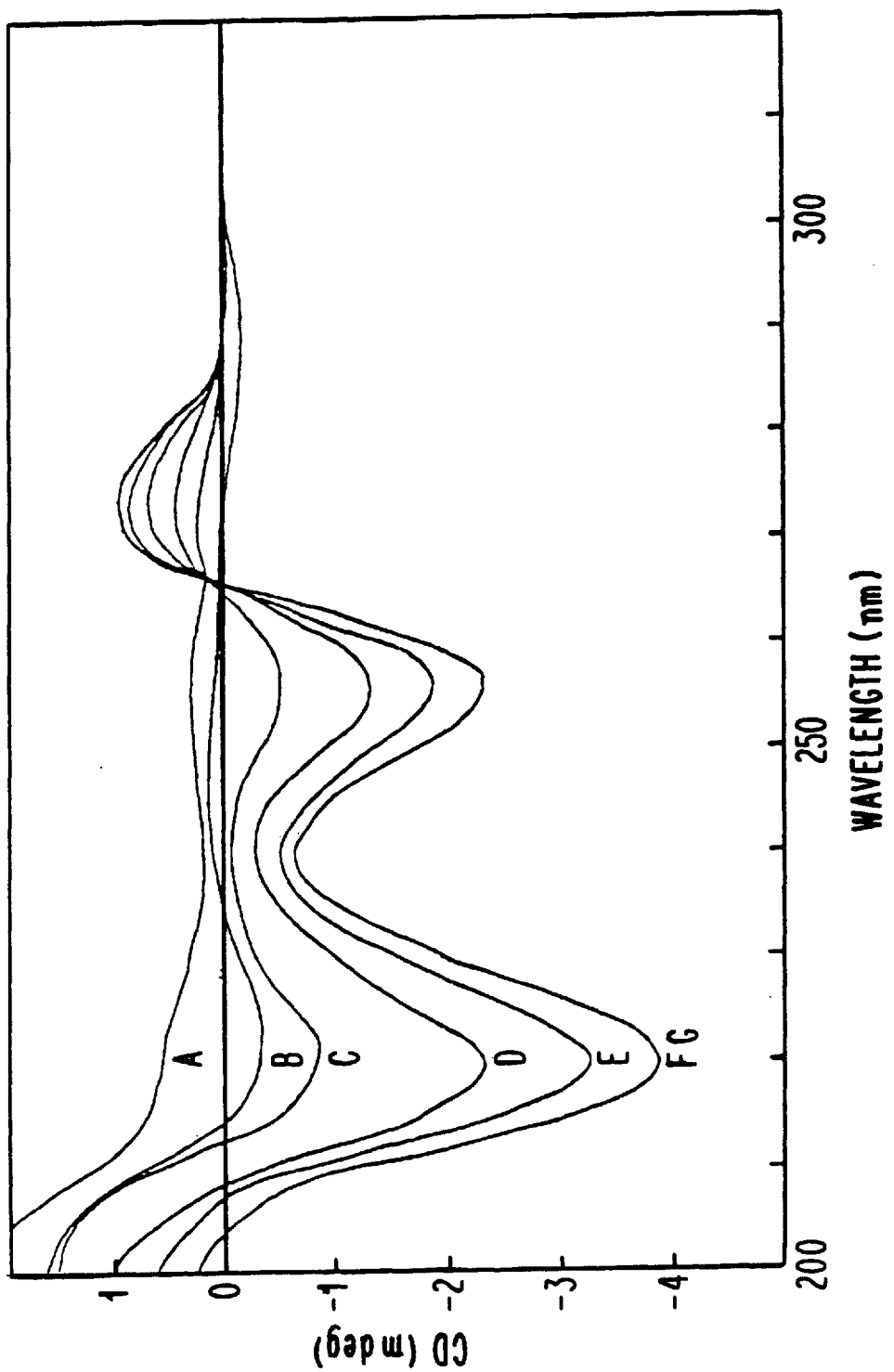
FIG. 1 is a plot showing titration to saturation of a 10 mer PNA to a complementary 10 mer PNA.

As can be seen in FIG. 1, the circular dichroism (CD) of PNA 10-mers of Example 1 are almost vanishingly small, indicating that there is no preferred helical stacking of bases. However, a strong CD spectrum arises upon titration of one 10-mer with the complementary 10-mer, a saturation obtained at about 1:1 stoichiometry, as shown in FIG. 2. The CD spectrum resembles that of B-DNA, indicating a right-handed helix. It is believed that a PNA-PNA complex having no preferred helicity initially is formed. The kinetics by which this double-stranded structure reorganizes into a uniform, right-handed double helix has been monitored and the activation parameters for the process determined.

Figure 3:
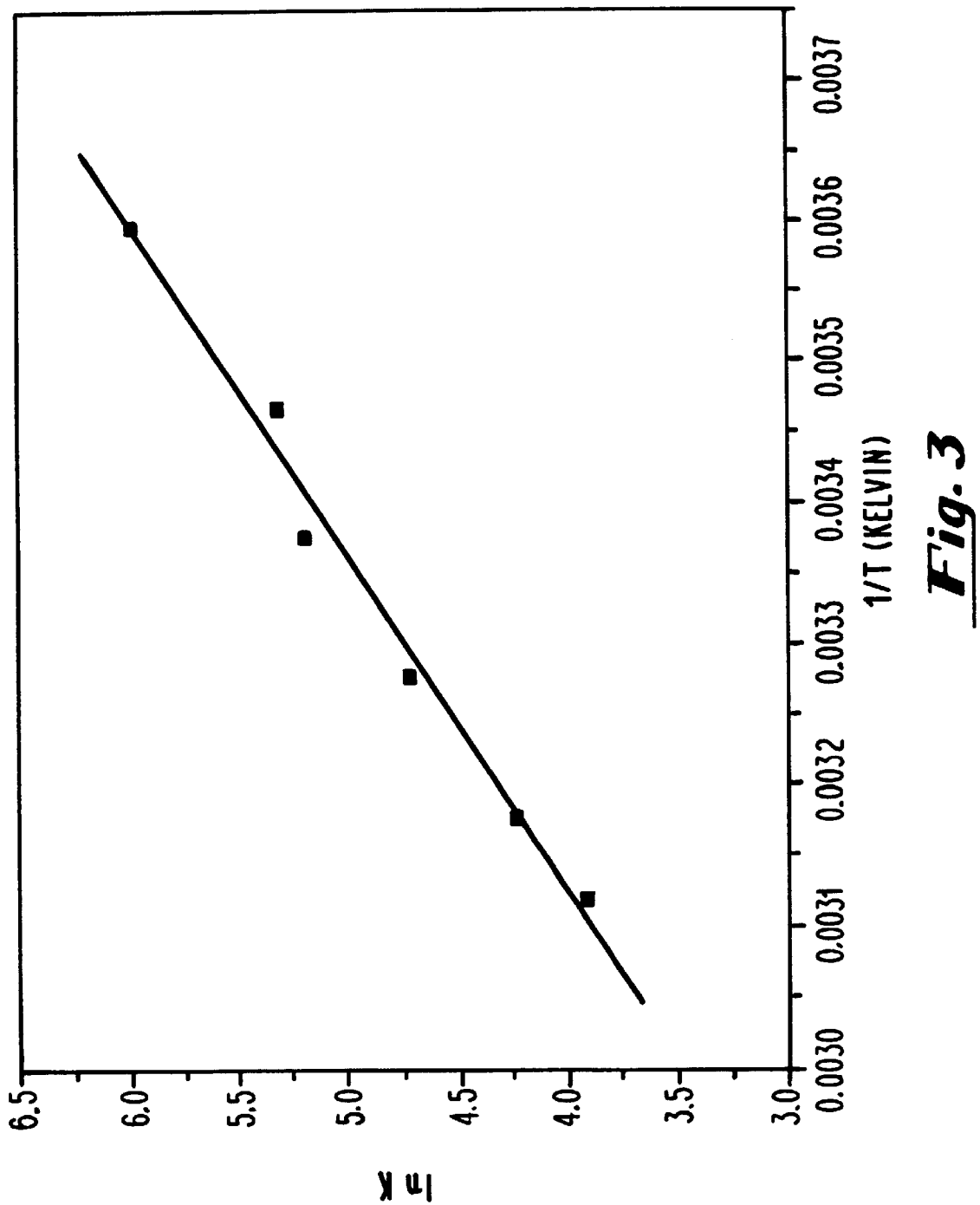
FIG. 3 is an Arrhenius plot of reaction rates at various temperatures during helical duplexation.

For DNA, circular dichroism in the nucleobase absorption region arises both from helical stacking of the bases, by excitation interactions between the neighboring bases, and from interactions with transitions of the chiral riboses moieties. In contrast, in PNA the electronic interaction between most of the bases and the chiral terminal lysine is negligible and the main source of circular dichroism is attributable almost solely to the chiral orientation of the base-pairs relative to each other. The right-handed helicity observed for PNA is determined by the chiral bias of a terminal lysine residue. The formation of a helical duplex between the two complementary PNA oligomers was slow enough to be followed by the increase in circular dichroism with time. This is in contrast with DNA-DNA duplex formation, which occurs within seconds. The development of circular dichroism follows first order reaction kinetics. Activation parameters have been determined by following the association at various temperatures, as shown in FIG. 3. Control experiments with different PNA concentrations gave identical results, confirming that the PNA-PNA association is fast and includes a reorganization process in an already base-paired complex. This observation is further supported by the absence of time dependent hypochromicity in normal absorption spectra. Such a reorganization in the corresponding cases of DNA-DNA and DNA-PNA decamers duplexes is too fast to be observed, indicating that the local chirality of the ribose in those cases immediately determines the handedness of base stacking. The conclusion is that the association of the two PNA-oligomers is fast in the base-pairing first step, but is followed by a slow seeding of the duplex chirality, from the terminal lysine residue, towards its right-handed helical structure. The activation energy obtained is 33.9 kJ/mole, which is low because the transition state is associated with a large negative entropy change ($\Delta S=-173$ kJ/mole; see, e.g., FIG. 3), implying a highly ordered transition state. This is a strong indication that the rate-limiting inversion step is a cooperative seeding of chirality from the terminal base-pairs involving the entire stack of bases.

We believe this is the first time a pure cooperative inversion transition in a nucleic acid-like structure has been isolated. Also, in contrast to DNA wherein ribose residues act as local chiral centers, optical activity of PNA-PNA duplexes is entirely a result of the helical arrangement of the nucleo-bases relative to each other. The CD spectrum can be compared with the theoretical and experimental spectra that have been generated for helix stacks of DNA bases to demonstrate the mimicry of DNA duplex structure. These PNA-PNA duplexes therefore are useful mimics of DNA for the purpose of modulating the expression or transcription of DNA and thus modulating a disease state to the benefit of a living organism.

The utility of these PNA-containing duplex structures can be illustrated by constructing PNA sequences which correspond to various sequences of the HIV TAR element that have the potential to form duplex structures either as stem-loop structures or two PNAs forming a duplex structure. In a competition assay, PNA structures that bind the tat transcription factor prevent binding of the competitor TAR sequence present in the incubation mixture. As the TAR RNA sequence is biotinylated only tat proteins available to bind to TAR will remain on the microtiter plate after washing away unbound molecules and tat protein complexed to a PNA sequence. The concentration dependence of the competition between the TAR PNA structures and biotinylated TAR structure will serve to define those sequences capable of effectively competing for tat and thus useful as HIV modulatory agents.

Additional objects, advantages, and novel features of this invention will become apparent to those skilled in the art upon examination of the following examples thereof, which are not intended to be limiting.

EXAMPLE 1

Synthesis of PNA Structures

PNA having formulas 1 through 5 above are prepared generally according to the synthetic protocols of our prior patent application WO 92/20702. Migration of the last nucleobase methylcarbonyl moiety to the terminal nitrogen is prevented by capping the N-terminus of the PNA chain with a glycine residue. The compounds are purified by HPLC (reverse phase, 0.1% trifluoroacetic acid in acetonitrile/water) and the composition verified by mass spectrometry.

EXAMPLE 2

Binding and Helix Formation of Complementary Antiparallel PNA Strands (FIG. 1)

The circular dichroism spectra of PNA-PNA mixtures were obtained by titrating PNA having sequence H-GTAGATCACT-LysNH$_2$ (PNA formula 1) with PNA having sequence H-AGTGATCTAC-LysNH$_2$ (PNA formula 2). The concentration of PNA formula 1 was held constant (50 μmole/L) and the concentration of PNA formula 2 was increased to provide the following formula 2:formula 1 stoichiometries: 0.25 (Curve C), 0.50 (Curve D), 0.75 (Curve E), 1.00 (Curve F), and 1.25 (Curve G). The hybridizations were performed in a 5 mmol/L sodium phosphate buffer, pH 7.0, at 20° C., after 20 minutes of incubation. The path length was 1 cm. Saturation was obtained at equimolar amounts of the two decamers.

FIG. 2 shows development of negative circular dichroism (at 220 nm) as a function of time after mixing equimolar amounts of PNA formula 1 with PNA formula 2. From top to bottom, the curves correspond to the following temperatures: 5° C., 15° C., 23° C., 32° C., 41° C., and 47° C.

FIG. 3 shows an Arrhenius plot of rates from the CD kinetics. The plot provides the activation energy as ΔH=33.9 kJ/mole (with the approximation that $(k_5T/h)exp(\Delta S^{\ddagger}/R)$ is constant). The full rate equation is $k=(k_3T/h)exp(-\Delta H^{\ddagger})exp(-\Delta S^{\ddagger}/R)$ then gives ΔS‡=−173 J/mole.

EXAMPLE 3

PNA Having Binding Affinity for The HIV-tat Protein as Measured in a Competitive Inhibition Assay Samples of PNAs corresponding to various TAR sequences prepared by the method of Example 1 are incubated with recombinant tat transcription factor (100 μM) for 15 minutes at room temperature at 1, 3, 10 ,30, and 100 μM (see, e.g., Cullen, et al., *Cell* 1990, 63, 655.). A competitor, a truncated version of the TAR sequence corresponding to residues 16–45 as a 2'-O-methyl oligonucleotide, is employed as a TAR sequence and is biotinylated at the 3'-O end by procedures generally in accordance with the protocols of application Ser. No. 08/032,852, Combinatorial Oligomer Immunoabsorbant Screening Assay For Transcription Factors And Other Biomolecule Binding, filed Mar. 16, 1993, the entire contents of which are incorporated herein by reference. This TAR sequence is added at 100 nM concentration. The reaction is incubated for 20 minutes and then added to streptavidin-coated microtiter plate wells. After unbound molecules are washed away with phosphate-buffered saline (PBS), 100 μL of 1:500 tat antisera is added to each well and incubated for 2 hours. Protein A/G antisera phosphatase is bound to the tat antibodies and PNPP (p-nitrophenylphosphate) substrate (200 μl) then is added. Color development is measured 2 hours later by reading absorbance at 405 nM on a Titertek Multiscan ELISA plate reader.

EXAMPLE 4

PNA Having Binding Affinity for the C-myc Protein

Myc-c is a nuclear protein involved in cell proliferation, differentiation, and neoplastic disease and binds DNA in a sequence specific manner. See, e.g., Nissen, *Cancer Research* 1986, 46, 6217 and Blackwell, *Science* 1990, 250, 1149. Crude nuclear extracts of myc-c are prepared generally in accordance with Franza, et al., *Nature* 1987, 330, 391, from HL 60 cells stimulated to induce the expression of myc-c.

Phosphorothioate oligonucleotides having the sequences GAT CCC CCC ACC ACG TGG TGC CTG A-B (SEQ ID NO:6) and GAT CTC AGG CAC CAC GTG GTG GGG G-B (SEQ ID NO:7), where B=biotin, are synthesized on an automated DNA synthesizer (Applied Biosystems model 380B) using modified standard phosphoramidite chemistry with oxidation by a 0.2M solution of 3H-1,2-benzodithiole-3-one 1,1-dioxide in acetonitrile for stepwise thiation of phosphite linkages. The thiation cycle wait step is 68 seconds and is followed by the capping step. β-Cyanoethyldiisopropyl phosphoramidites can be purchased from Applied Biosystems (Foster City, Calif.). Bases are deprotected by incubation in methanolic ammonia overnight. Following base deprotection, the oligonucleotides are dried in vacuo. Removal of 2'-hydroxyl t-butyldimethylsilyl protecting groups is effected by incubating the oligonucleotide in 1M tetrabutylammonium fluoride in tetrahydrofuran overnight. The RNA oligonucleotides are further purified on C$_{18}$ Sep-Pak cartridges (Waters, Division of Millipore Corp., Milford, Mass.) and ethanol precipitated. The phosphorothioate oligonucleotides are hybridized to create the double stranded NF-kB binding site.

A series of PNA-PNA duplexes is synthesized and hybridized to give a new series of PNA duplexes corresponding to different length portions of the myc-c binding sequence. Each duplex is incubated in triplicate at concentrations of 1, 3, 10, 30, and 100 μM with the HL-60 extract described above. The myc P=S binding site then is added and the mixtures are incubated and washed with PBS. An antibody directed to the leucine zipper region of the myc protein (Santa Cruz Biotechnology) is added at a 1:1000 dilution. Non-bound molecules are washed away with PBS. Binding of myc to biotinylated c-myc transcription factor is quantitated by adding 100 µl of 1:500 tat antisera to each well for 2 hours. Protein A/G-alkaline phosphatase (Pierce; 1:5000; 100 µl) then is added and any excess is removed by washing with PBS. PNPP substrate (200 µl) then is added. Color development is measured 2 hours later by reading absorbance at 405 nM on a Titertek Multiscan ELISA plate reader.

EXAMPLE 5

PNA Having Binding Affinity for the C-rel Transcription Factor

C-rel has been shown to represent a constituent of the NF-kB site binding transcription factor, which plays a crucial role in the expression of a number of genes including the immunoglobulin k light chain gene, IL-2ra, and MHC. (see, e.g., Gilmore, et al., *Cell* 1986, 62, 791.)

Crude nuclear extracts are prepared as detailed by Franza, et al., *Nature* 1987, 330, 391, from Jurkat cells stimulated 4 hours with 1 µM PHA and 100 nM PMA to induce the expression of rel. The extract is then preabsorbed with 100 µl streptavidin agarose per ml for 10 minutes. This is followed with the addition of poly dI.dC as a nonspecific competitor at a concentration of 100 µg/ml of extract. Nuclear extracts containing the biotinylated NF-kB binding site competitor are prepared as in Example 4, above.

A series of PNA duplexes is synthesized to correspond to various length fragments of the consensus binding sequence of c-rel. NF-kB binding site competitor is added to each duplex and the resulting samples are washed. Antibody directed to rel is added. The amount of rel bound is quantitated by adding 100 µl of 1:500 rel antisera to each well for 2 hours. Protein A/G-alkaline phosphatase (Pierce; 1:5000; 100 µl) the is added and any excess is removed by washing with PBS. PNPP substrate (200 µl) then is added. Color development is measured 2 hours later by reading absorbance at 405 nM on a Titertek Multiscan ELISA plate reader.

EXAMPLE 6

PNA Having Binding Affinity for the AP-1 Transcription Factor

Genes belonging to the fos and jun oncogene families encode nuclear proteins associated with a number of transcriptional complexes, see, e.g. , Konig, et al. , *EMBO Journal* 1989, 8, 2559. C-jun is a major component of the AP-1 binding site, which was originally shown to regulate tissue plasminogen activator (TPA) induced expression of responsive genes through the TPA response element (TRE). The jun protein forms homo- or heterodimers which bind the TRE. The fos protein is only active as a heterodimer with any of the jun family of proteins. Fos/jun heterodimers have a much higher affinity for the TRE than jun homodimers.

Both the fos and the jun cDNA have been cloned downstream of the Sp6 promoter. RNA is produced from each plasmid in vitro, then used to produce functional jun and fos proteins in rabbit reticulocyte lystates. The fos and jun proteins are then allowed to bind to the biotinylated AP-1 binding site in competition with PNA duplex sequences constructed as mimics of the proper consensus sequence for binding fos and jun, CGC TTG GTG ACT CAG CCG GAA. Binding is quantitated with an antibody directed to fos or jun. When the fos alone is incubated with the AP-1 site there will be no detectable binding with either antibody. When the jun alone is incubated with the binding site, a signal will be detected with only the jun antibody. This is consistent with the formation of a jun homodimer, which has previously been demonstrated to bind AP-1. When the fos and jun proteins are mixed a signal will be detected with both fos and jun antibodies. This is consistent with the formation of a fos/jun homodimer which is known to bind the AP-1 site and should be detectable with either antibody.

PNA sequences of the present invention can be tested for the ability to block the formation of the fos/jun heterodimer. Molecules which block formation will decrease the signal detected with the fos antibody, but not the jun antibody.

EXAMPLE 7

Chimera Macromolecule Having Peptide Nucleic Acids Section Attaching to 3' Terminus of a 2'-Deoxy Phosphorothioate Oligonucleotide Section A first section of peptide nucleic acids is prepared as per PCT patent application WO 92/20702. The peptide nucleic acids are prepared from the C terminus towards the N terminus using monomers having protected amino groups. Following completion of the peptide region, the terminal amine blocking group is removed and the resulting amine reacted with a 3'-C-(formyl)-2',3'-dideoxy-5'-trityl nucleotide as prepared per the procedure of Vasseur, et. al., *J. Am. Chem. Soc.* 1992, 114, 4006. The condensation of the amine with the aldehyde moiety of the C-formyl nucleoside is effected as per the conditions of the Vasseur, ibid., to yield an intermediate imine linkage. The imine linkage is reduced under reductive the alkylation conditions of Vasseur, ibid., with HCHO/NaBH$_3$CN/AcOH to yield the nucleoside connected to the peptide nucleic acid via an methyl alkylated amine linkage. An internal 2'-deoxy phosphorothioate nucleotide region is then continued from this nucleoside as per standard automatated DNA synthetic protocols (see Oligonucleotide synthesis, a practic approach, M. J. Gait ed, IRL Press, 1984).

EXAMPLE 8

Chimera Macromolecule Having Peptide Nucleic Acids Section Attaching to 5' Terminus of a Phosphorothioate Oligonucleotide Section A phosphorothioate oligonucleotide is prepared in the standard manner on a solid support as per standard protocols (see Oligonucleotides and Analogues, A Practical Approach, F. Eckstein Ed., IRL Press, 1991. The dimethoxytrityl blocking group on that nucleotide is removed in the standard manner. Peptide synthesis for the peptide region is commenced by reaction of the carboxyl end of the first peptide nucleic acid of this region with the 5' hydroxy of the last nucleotide of the DNA region. Coupling is effected via EDC (Pierce) in pyridine to form an ester linkage between the peptide and the nucleoside. Peptide synthesis is then continued in the manner of patent application WO 92/20702 to complete the peptide nucleic acid region.

EXAMPLE 9

Double Stranded Structures that Include Chimera Strand

Duplex structures will be formed with the chimera strands of Examples 7 and 8. Duplex structures can include duplexes between a PNA-RNA or PNA-DNA strand and a RNA strand, a PNA-RNA or PNA-DNA strand and a DNA strand, a PNA-RNA or PNA-DNA strand and a PNA strand or a PNA-RNA or PNA-DNA strand and a further chimeric PNA-DNA or PNA-RNA strand.

EXAMPLE 10

Binding Between PNA Containing Double Stranded Structure and Transcription Factor or Other Protein A double stranded PNA structure, a structure containing PNA chimeric strand and a nucleic acid strand or two PNA chimera strands will be used to bind to or otherwise modulate single stranded DNA, double stranded DNA, RNA, a transcription factor or other protein. In the use of a PNA containing chimera, part of the binding between the chimera and the transcription factor or other protein can include binding between the sugar-phosphate backbone of the DNA or RNA portion of the chimera and hydrogen bonding between the ligands, e.g. nucleobases, of the PNA portion of the chimera. Binding to the sugar-phosphate backbone includes binding to phosphodiester linkages, phosphorothioate linkages or other linkgages that may be used as the bacbone of the DNA or RNA. In other instances, bonding can include hydrophobic contacts between hydrophobic groups on the ligands, including nucleobases, of the PNA or the nucleobases of the nucleic acid portion of the chimera with like hydrophobic groups on proteins that are being bound. Such hydrophobic groups on the chimeric strand include the methyl groups on thymine nucleobases.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A process comprising the steps of:
providing a cell comprising a transcription factor;
forming a double-stranded structure by:
providing a first strand and a second strand, each strand comprising a peptide nucleic acid moiety that includes a sequence of ligands covalently bound by linking moieties, wherein at least a portion of said ligands bind said transcription factor; and
disposing said strands relative to one another to form hydrogen bonds therebetween and thereby form a double strand; and
introducing said double-stranded structure into said cell.

2. The process of claim 1 wherein at least two of said linking moieties in a strand have both amino ends and carboxyl ends and said linking moieties are covalently bound via amide linkages.

3. The process of claim 2 wherein each of said linking moieties includes a nitrogen atom between said amino end and said carboxyl end.

4. The process of claim 3 wherein each of said ligands is connected to said linking moieties via said nitrogen atoms.

5. The process of claim 1 wherein at least one of said strands has the formula:

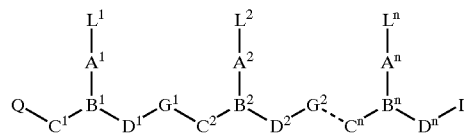

wherein:
n is at least 2,
each of $L^1-L^n$ is independently selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, heterocyclic moieties, and reporter ligands;
each of $C^1-C^n$ is $(CR^6R^7)_y$, where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined above, and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;

each of $D^1-D^n$ is $(CR^6R^7)_z$ where $R^6$ and $R^7$ are as defined above;
each of y and z is zero or an integer from 1 to 10, the sum y+z being greater than 2 but not more than 10;
each of $G^1-G^{n-1}$ is $-NR^3CO-$, $-NR^3CS-$, $-NR^3SO-$ or $-NR^3SO_2-$, in either orientation, where $R^3$ is as defined above;
each of $A^1-A^n$ and $B^1-B^n$ are selected such that:
(a) A is a group of formula (IIa), (IIb) or (IIc), and B is N or $R^3N^+$; or
(b) A is a group of formula (IId) and B is CH;

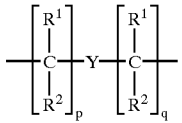   (IIa)

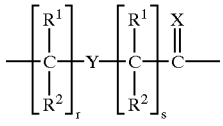   (IIb)

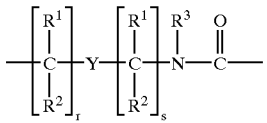   (IIc)

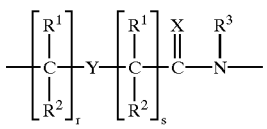   (IId)

where:
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, $(C_1-C_4)$ alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, $(C_1-C_4)$ alkyl, hydroxy- or alkoxy- or alkylthio-substituted $(C_1-C_4)$alkyl, hydroxy, alkoxy, alkylthio and amino;

Q is —$CO_2H$, —$CONR'R''$, —$SO_3H$ or —$SO_2NR'R''$ or an activated derivative of —$CO_2H$ or —$SO_3H$; and I is —$NHR'''R''''$ or —$NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, nucleosides, nucleotides, nucleotide diphosphates, nucleotide triphosphates, oligonucleotides, oligonucleosides and soluble and non-soluble polymers.

6. The process of claim 5 wherein each of said first and second polymeric strands comprises a moiety of the formula:

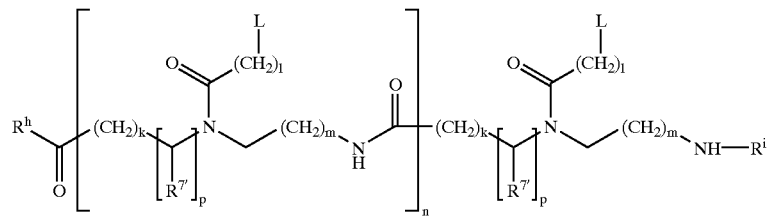

or the formula

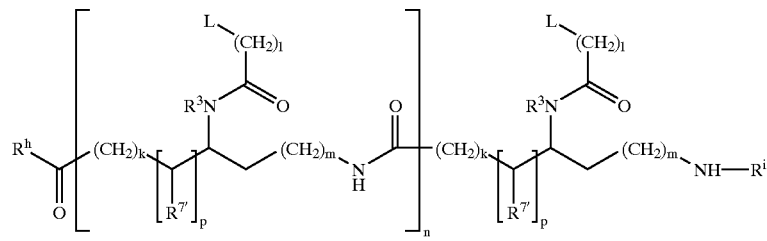

or the formula

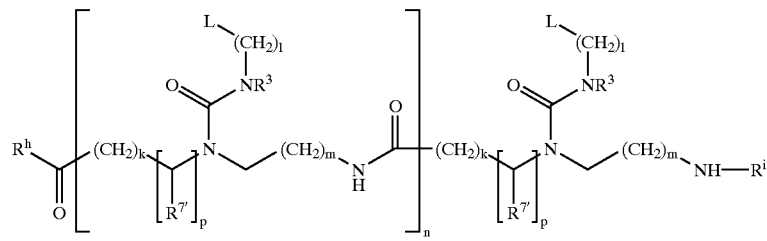

wherein:

each L is independently selected from the group consisting of hydrogen, phenyl, heterocyclic moieties, naturally occurring nucleobases, and non-naturally occurring nucleobases;

each $R^{7'}$ is independently selected from the group consisting of hydrogen and the side chains of naturally occurring alpha amino acids;

n is an integer greater than 1, each k, l, and m is, independently, zero or an integer from 1 to 5;

each p is zero or 1;

$R^h$ is OH, $NH_2$ or —$NHLysNH_2$; and $R^i$ is H or $COCH_3$.

* * * * *

UNITED STATES PATENT AND TRADEMARK OFFICE
CERTIFICATE OF CORRECTION

PATENT NO. : 6,610,650 B1
DATED : August 26, 2003
INVENTOR(S) : Norden et al.

It is certified that error appears in the above-identified patent and that said Letters Patent is hereby corrected as shown below:

Title page,
Item [60], Related U.S. Application Data, please delete "May 19, 1992" and insert
-- May 22, 1992 --

Column 1,
Line 12, please delete "May 19, 1992" and insert -- May 22, 1992 --

Signed and Sealed this

Twenty-ninth Day of March, 2005

JON W. DUDAS
*Director of the United States Patent and Trademark Office*